US012308123B1

United States Patent
Shu et al.

(10) Patent No.: US 12,308,123 B1
(45) Date of Patent: May 20, 2025

(54) ELECTROCARDIOGRAM (ECG) SIGNAL CLASSIFICATION METHOD BASED ON CONTRASTIVE LEARNING AND MULTI-SCALE FEATURE EXTRACTION

(71) Applicants: Qilu University of Technology (Shandong Academy of Sciences), Jinan (CN); Shandong Artificial Intelligence Institute, Jinan (CN); SHANDONG COMPUTER SCIENCE CENTER (NATIONAL SUPERCOMPUTING CENTER IN JINAN), Jinan (CN)

(72) Inventors: Minglei Shu, Jinan (CN); Luyao Li, Jinan (CN); Pengyao Xu, Jinan (CN); Shuwang Zhou, Jinan (CN); Zhaoyang Liu, Jinan (CN)

(73) Assignees: QILU UNIVERSITY OF TECHNOLOGY (SHANDONG ACADEMY OF SCIENCES), Jinan (CN); SHANDONG ARTIFICIAL INTELLIGENCE INSTITUTE, Jinan (CN); SHANDONG COMPUTER SCIENCE CENTER (NATIONAL SUPERCOMPUTING CENTER IN JINAN), Jinan (CN)

( * ) Notice: Subject to any disclaimer, the term of this patent is extended or adjusted under 35 U.S.C. 154(b) by 0 days.

(21) Appl. No.: 18/664,289

(22) Filed: May 15, 2024

(30) Foreign Application Priority Data

Nov. 16, 2023 (CN) .......................... 202311523667.5

(51) Int. Cl.
*G16H 50/20* (2018.01)
(52) U.S. Cl.
CPC .................................. *G16H 50/20* (2018.01)

(58) Field of Classification Search
CPC ...................................................... G16H 50/20
See application file for complete search history.

(56) References Cited

U.S. PATENT DOCUMENTS

2022/0378379 A1* 12/2022 Zimmerman ........ A61B 5/7275
2022/0384044 A1* 12/2022 Ulloa-Cerna ........ A61B 5/7275
(Continued)

FOREIGN PATENT DOCUMENTS

AU     2020103901 A4    2/2021
CN      110309758 A    10/2019
(Continued)

OTHER PUBLICATIONS

Li Wenhao, The Research and Application on Incorporating Domain Knowledge into Deep Learning for Heartbeat Anomaly Detection, Beijing Jiaotong University, 2022, pp. 1-56.

*Primary Examiner* — Jay M. Patel
(74) *Attorney, Agent, or Firm* — Bayramoglu Law Offices LLC (57) ABSTRACT

An electrocardiogram (ECG) signal classification method based on contrastive learning and multi-scale feature extraction are provided. A squeeze-and-excitation-residual networks with next-generation aggregated transformations-context-aware network (SE-ResNeXt-CAN) network model includes a shallow feature extraction module, a first squeeze-and-excitation residual module (SERM), a second SERM, a first context-aware residual module (CARM), and a second CARM. Through the combination and optimization of these modules, the SE-ResNeXt-CAN network model adaptively learns a correlation between channels, and expands a receptive field to fully capture a key feature, improving the performance and generalization ability of an ECG signal classification task.

5 Claims, 10 Drawing Sheets

(56) References Cited

U.S. PATENT DOCUMENTS

2023/0238134 A1* 7/2023 Ravishankar .......... A61B 5/361
                                                    600/518
2023/0335244 A1* 10/2023 Hagenbrock .......... G16H 10/60

FOREIGN PATENT DOCUMENTS

| CN | 116028858 A | 4/2023 |
| CN | 116975600 A | 10/2023 |
| WO | 2022193312 A1 | 9/2022 |

* cited by examiner

FIG. 8 though content begins here based on page layout:

ELECTROCARDIOGRAM (ECG) SIGNAL CLASSIFICATION METHOD BASED ON CONTRASTIVE LEARNING AND MULTI-SCALE FEATURE EXTRACTION

CROSS-REFERENCE TO THE RELATED APPLICATIONS

This application is based upon and claims priority to Chinese Patent Application No. 202311523667.5, filed on Nov. 16, 2023, the entire contents of which are incorporated herein by reference.

TECHNICAL FIELD

The present disclosure relates to the technical field of electrocardiogram (ECG) signal classification, and in particular to an ECG signal classification method based on contrastive learning and multi-scale feature extraction.

BACKGROUND

The heart's electrical activity is represented by electrical signals. The electrical signals are acquired by electrodes placed in specific positions on the body and are presented in the form of an electrocardiogram (ECG). Due to its non-invasive and real-time characteristics, ECG is often involved in classifying electrical signals of the heart. An ECG signal classification method based on contrastive learning can acquire useful features based on data characteristics, without the need for pre-training through pre-labeled data. However, traditional network models still have shortcomings in ECG signal classification. For example, traditional network models cannot achieve sufficient processing of features from different channels and are unable to adaptively learn the correlation among channels. In addition, traditional network models are limited by a small receptive field and cannot fully capture the contextual information of the ECG signal.

SUMMARY

In order to overcome the above technical shortcomings, the present disclosure provides an electrocardiogram (ECG) signal classification method based on contrastive learning and multi-scale feature extraction, which can improve the performance and generalization ability of an ECG signal classification task.

The technical solution used in the present disclosure to resolve the technical problem thereof is as follows:

The ECG signal classification method based on contrastive learning and multi-scale feature extraction includes the following steps:

a) dividing an ECG signal dataset into K batches, each batch including T signals forming an ECG signal set X, $X=\{X_1, X_2, \ldots, X_i, \ldots, X_T\}$, where $X_i$ denotes an i-th ECG signal, $i \in \{1, \ldots, T\}$.

b) performing data augmentation on the i-th ECG signal $X_i$ to acquire a sample $X_i^{M1}$;

c) constructing a squeeze-and-excitation-residual networks with next-generation aggregated transformations-context-aware network (SE-ResNeXt-CAN) network model, including a shallow feature extraction module, a first squeeze-and-excitation residual module (SERM), a second SERM, a first context-aware residual module (CARM), and a second CARM;

d) inputting the sample $X_i^{M1}$ into the shallow feature extraction module of the SE-ResNeXt-CAN network model to acquire a feature $f^1$;

e) inputting the feature $f^1$ into the first SERM of the SE-ResNeXt-CAN network model to acquire a feature $f^2$;

f) inputting the feature $f^2$ into the second SERM of the SE-ResNeXt-CAN network model to acquire a feature $f^3$;

g) inputting the feature $f^3$ into the first CARM of the SE-ResNeXt-CAN network model to acquire a feature $f^4$;

h) inputting the feature $f^4$ into the second CARM of the SE-ResNeXt-CAN network model to acquire a feature $f^5$;

i) constructing a first multilayer perceptron, including a flattening layer, a first fully connected layer, and a second fully connected layer in sequence; and inputting the feature $f^5$ into the first multilayer perceptron to acquire a feature $h_i$;

j) training the SE-ResNeXt-CAN network model to acquire an optimized SE-ResNeXt-CAN network model;

k) dividing a new ECG signal dataset into K batches, each batch including T signals forming an ECG signal set Y, $Y=\{Y_1, Y_2, \ldots, Y_i, \ldots, Y_N\}$, where denotes an i-th ECG signal, $i \in \{1, \ldots, T\}$; and n) inputting the i-th ECG signal $Y_i$ into the optimized SE-ResNeXt-CAN network model to acquire a feature $f^{5'}$; constructing a second multilayer perceptron, including a flattening layer, a first fully connected layer, a rectified linear unit (Relu) activation function layer, and a second fully connected layer in sequence; inputting the feature $f^{5'}$ into the second multilayer perceptron to acquire a feature $f^{5''}$; and inputting the feature $f^{5''}$ into a softmax activation function to acquire a probability distribution $z_i$ of the i-th ECG signal $Y_i$, where the probability distribution $z_i$ is a classification result of the ECG signal.

Further, in the step a), the ECG signal dataset is a PTB-XL dataset, and the T signals in each batch are sampled at a rate of 500 Hz, with duration of 10 s.

Further, step b) includes the following steps:

b-1) generating, by an np.random.normal function in Python, Gaussian noise with a mean of 0, a variance of 0.01, and a same size as the i-th ECG signal $X_i$; and b-2) adding the Gaussian noise to the i-th ECG signal $X_i$ to acquire the sample $X_i^{M1}$.

Further, the step d) includes:

d-1) constructing the shallow feature extraction module of the SE-ResNeXt-CAN network model, including a convolutional layer, a Batch_Norm layer, a Relu activation function, and a Dropout layer in sequence; and inputting the sample $X_i^{M1}$ into the shallow feature extraction module to acquire the feature $f^1$.

Further, the step e) includes the following steps:

e-1) constructing the first SERM of the SE-ResNeXt-CAN network model, including a residual module (RM) and an excitation and convolution module;

e-2) constructing the RM of the first SERM, including a first branch and a second branch; constructing the first branch of the RM, including a first convolutional layer, a second convolutional layer, a first batch normalization (BN) layer, a Relu activation function, a third convolutional layer, a second BN layer, and a Dropout layer in sequence; inputting the feature $f^1$ into the first branch of the RM to acquire a feature $f_1^2$; constructing the second branch of the RM, including a max pooling layer and a convolutional layer in sequence; inputting the feature $f^1$ into the second branch of the RM to acquire a feature $f_2^2$; and adding the feature $f_1^2$ and the feature $f_2^2$ to acquire a feature $rm^1$;

e-3) constructing the excitation and convolution module, including a first convolutional layer, a first SE module, a second convolutional layer, a second SE module, a third convolutional layer, and a third SE module in sequence; and inputting the feature $f^1$ into the excitation and convolution module to acquire a feature $f_3^2$; and e-4) adding the feature $rm^1$ and the feature $f_3^2$ to acquire the feature $f^2$.

Further, the step f) includes:

f-1) constructing the second SERM of the SE-ResNeXt-CAN network model, including a RM and an excitation and convolution module;

f-2) constructing the RM of the second SERM, including a first branch and a second branch; constructing the first branch of the RM, including a first convolutional layer, a second convolutional layer, a first batch normalization (BN) layer, a Relu activation function, a third convolutional layer, a second BN layer, and a Dropout layer in sequence; inputting the feature $f^2$ into the first branch of the RM to acquire a feature $f_1^3$; constructing the second branch of the RM, including a max pooling layer and a convolutional layer in sequence; inputting the feature $f^2$ into the second branch of the RM to acquire a feature $f_2^3$; and adding the feature $f_1^3$ and the feature $f_2^3$ to acquire a feature $rm^2$;

f-3) constructing the excitation and convolution module, including a first convolutional layer, a first SE module, a second convolutional layer, a second SE module, a third convolutional layer, and a third SE module in sequence; and inputting the feature $f^2$ into the excitation and convolution module to acquire a feature $f_3^3$; and f-4) adding the feature $rm^2$ and the feature $f_3^3$ to acquire the feature $f^3$.

Further, the step g) includes:

g-1) constructing the first CARM of the SE-ResNeXt-CAN network model, including a RM, a dilated convolution module, and a channel attention module;

g-2) constructing the RM of the first CARM, including a first branch and a second branch; constructing the first branch of the RM, including a first convolutional layer, a BN layer, a first Relu activation function, a second convolutional layer, a second Relu activation function, and a Dropout layer in sequence; inputting the feature $f^3$ into the first branch of the RM to acquire a feature $f_1^4$; constructing the second branch of the RM, including a convolutional layer; inputting the feature $f^3$ into the second branch of the RM to acquire a feature $f_2^4$; adding the feature $f_1^4$ and the feature $f_2^4$ to acquire a feature $rm^3$;

g-3) constructing the dilated convolution module of the first CARM, including a first dilated convolution layer, a first convolutional layer, a second dilated convolution layer, a second convolutional layer, and a Relu activation function in sequence; inputting the feature $f^3$ into the dilated convolution module to acquire a feature $f_3^4$; and adding the feature $rm^3$ and the feature $f_3^4$ to acquire a feature $pcdc^1$;

g-4) constructing the channel attention module of the first CARM, including a convolutional layer, an average pooling layer, a first fully connected layer, and a second fully connected layer in sequence; and inputting the feature $f^3$ into the channel attention module to acquire a feature $f_4^4$; and g-5) multiplying the feature $pcdc^1$ by the feature $f_4^4$ to acquire the feature $f^4$.

Further, the step h) includes:

h-1) constructing the second CARM of the SE-ResNeXt-CAN network model, including a RM, a dilated convolution module, and a channel attention module;

h-2) constructing the RM of the second CARM, including a first branch and a second branch; constructing the first branch of the RM, including a first convolutional layer, a BN layer, a first Relu activation function, a second convolutional layer, a second Relu activation function, and a Dropout layer in sequence; inputting the feature $f^4$ into the first branch of the RM to acquire a feature $f_1^5$; constructing the second branch of the RM, including a convolutional layer; inputting the feature $f^4$ into the second branch of the RM to acquire a feature $f_2^5$; adding the feature $f_1^5$ and the feature $f_2^5$ to acquire a feature $rm^4$;

h-3) constructing the dilated convolution module of the second CARM, including a first dilated convolution layer, a first convolutional layer, a second dilated convolution layer, a second convolutional layer, and a Relu activation function in sequence; inputting the feature $f^4$ into the dilated convolution module to acquire a feature $f_3^5$; and adding the feature $rm^4$ and the feature $f_3^5$ to acquire a feature $pcdc^2$;

h-4) constructing the channel attention module of the second CARM, including a convolutional layer, an average pooling layer, a first fully connected layer, and a second fully connected layer in sequence; and inputting the feature $f^4$ into the channel attention module to acquire a feature f; and h-5) multiplying the feature $pcdc^2$ by the feature $f_4^5$ to acquire the feature $f^5$.

Further, the step j) includes: training, by an adaptive moment estimation (Adam) optimizer, the SE-ResNeXt-CAN network model through an NT-Xent loss function to acquire the optimized SE-ResNeXt-CAN network model.

Further, in the step k), the new ECG signal dataset is a China Physiological Signal Challenge (CPSC) dataset, and the T signals in each batch are sampled at a rate of 500 Hz, with duration of 10 s.

The present disclosure has the following beneficial effects. The SE-ResNeXt-CAN network model includes five modules. The first module is a shallow feature extraction module, which is configured to extract a shallow feature. The second module is a first SERM, including a RM and an excitation and convolution module in parallel. The third module is a second SERM, including a RM and an excitation and convolution module in parallel. The SE module adaptively learns the correlation between channels and assigns different weights to features of different channels, thereby improving the effectiveness and discriminability of feature representation and enhancing the expression ability of the model. The SE module and convolution are combined in series, which can reduce the total number of parameters in the network. Compared with parallel combination, the serial combination can utilize the parameters of the model efficiently while maintaining certain performance. The fourth module is a first CARM, including a dilated convolution module, a RM, and a channel attention module in parallel. The fifth module is a second CARM, including a dilated convolution module, a RM, and channel attention module in parallel. The dilated convolution module can learn features of different receptive fields, thereby improving the diversity and richness of feature extraction. The parallel operation can simultaneously acquire feature information at multiple scales, thereby capturing feature representations at different levels. The RM can maintain the integrity and consistency of the feature and prevent problems such as gradient vanishing. The channel attention module adaptively learns the correlation between channels and assigns different weights to different channels. The design improves the effectiveness and discriminability of feature representation, enabling the model to focus on important feature channels, thereby enhancing the expression ability of the model. In the present disclosure, through the combination of these modules, the ECG signal classification method based on contrastive learning and multi-scale feature extraction can well capture key features of the ECG signal, thereby improving classification accuracy and robustness.

DETAILED DESCRIPTION OF THE EMBODIMENTS

Figure 1:
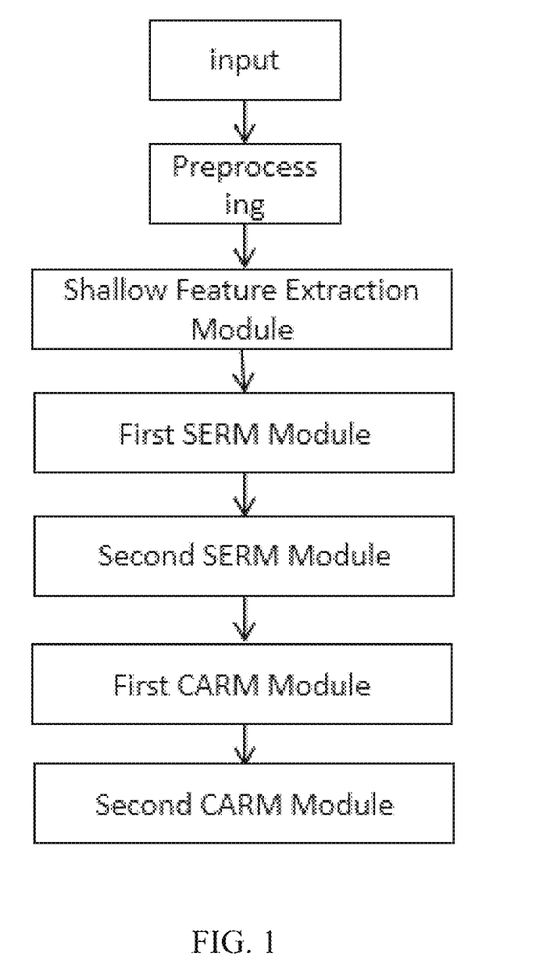
FIG. 1 is a flowchart of a method according to the present disclosure.
Figure 2:
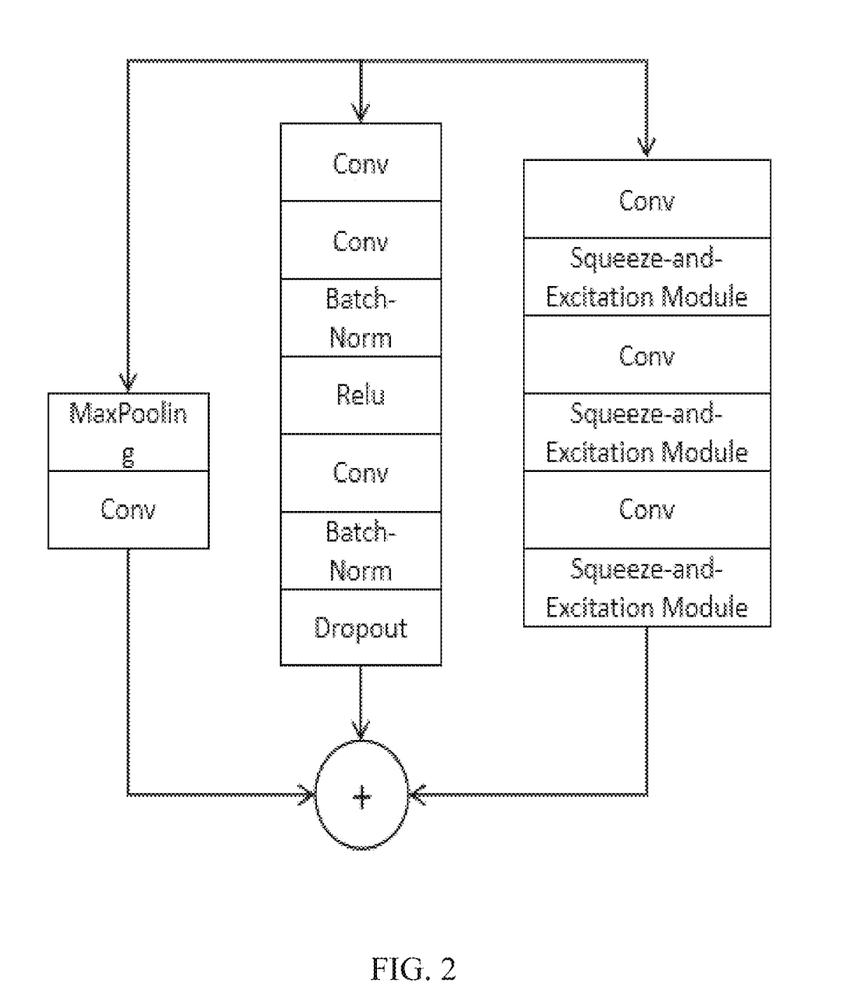
FIG. 2 is a structural diagram of a squeeze-and-excitation residual module (SERM) according to the present disclosure.
Figure 3:
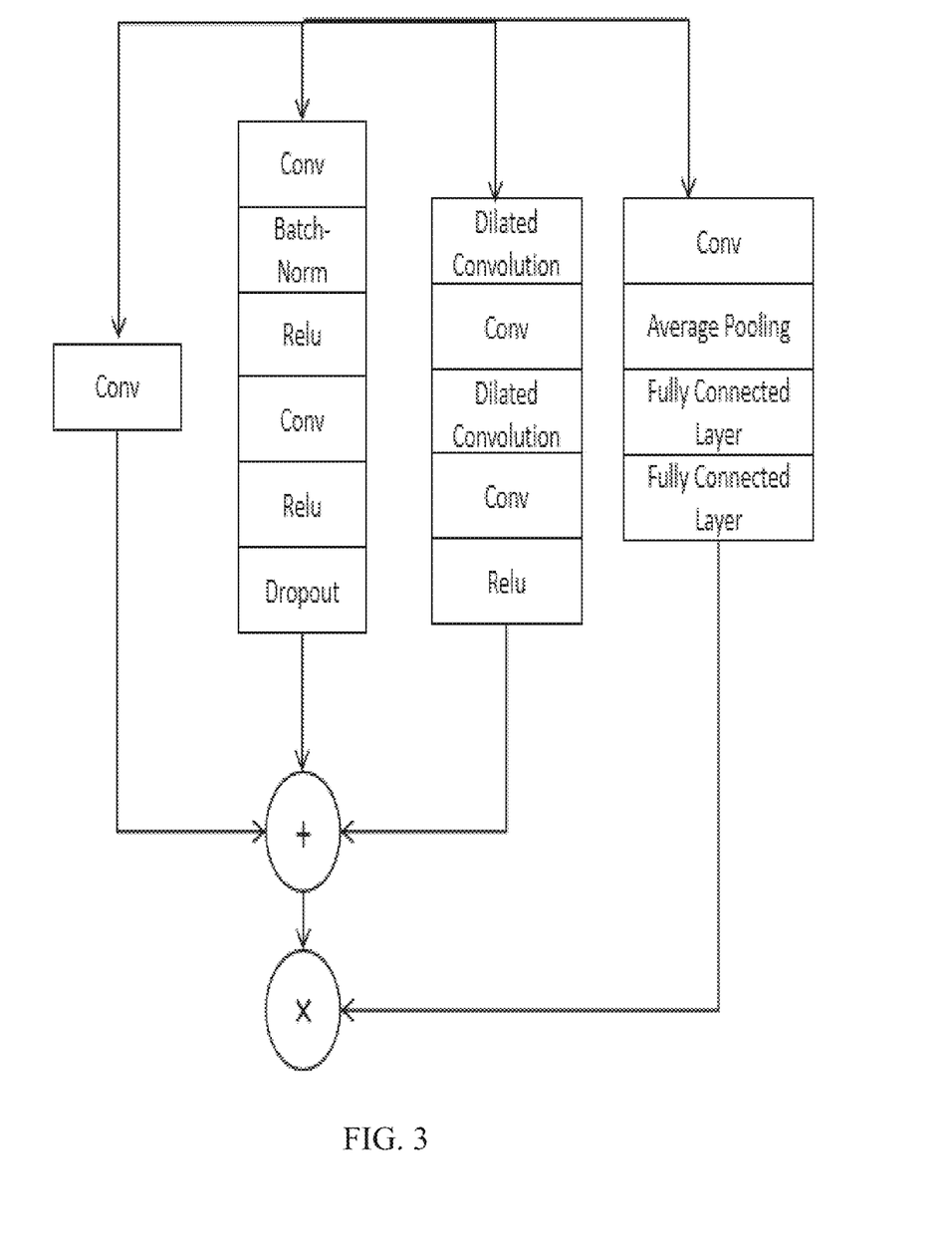
FIG. 3 is a structural diagram of a context-aware residual module (CARM) according to the present disclosure.

The present disclosure is further described below with reference to FIG. 1, FIG. 2, and FIG. 3.

An electrocardiogram (ECG) signal classification method based on contrastive learning and multi-scale feature extraction includes the following steps.
a) An ECG signal dataset is divided into K batches, each batch including T signals forming ECG signal set X, X={$X_1, X_2, \ldots, X_i, \ldots, X_T$}, where $X_i$ denotes an i-th ECG signal, i∈{1, . . . , T}.
b) Data augmentation is performed on the i-th ECG signal $X_i$ to acquire sample $X_i^{M1}$.
c) A squeeze-and-excitation-residual networks with next-generation aggregated transformations-context-aware network (SE-ResNeXt-CAN) network model is constructed, including a shallow feature extraction module, a first squeeze-and-excitation residual module (SERM), a second SERM, a first context-aware residual module (CARM), and a second CARM. The combination of these five modules improves the feature extraction ability and enables hierarchical feature representation, thereby enhancing the performance and generalization ability of the model and improving the performance of downstream classification tasks.
d) The sample $X_i^{M1}$ is input into the shallow feature extraction module of the SE-ResNeXt-CAN network model to acquire feature $f^1$.
e) The feature $f^1$ is input into the first SERM of the SE-ResNeXt-CAN network model to acquire feature $f^2$.
f) The feature $f^2$ is input into the second SERM of the SE-ResNeXt-CAN network model to acquire feature $f^3$.
g) The feature $f^3$ is input into the first CARM of the SE-ResNeXt-CAN network model to acquire feature $f^4$.
h) The feature $f^4$ is input into the second CARM of the SE-ResNeXt-CAN network model to acquire feature $f^5$.
i) A first multilayer perceptron is constructed, including a flattening layer, a first fully connected layer, and a second fully connected layer in sequence; and the feature $f^5$ is input into the first multilayer perceptron to acquire feature $h_i$. The first fully connected layer in the first multilayer perceptron includes 64 neurons, and the second fully connected layer in the first multilayer perceptron includes 32 neurons. The feature $h_i$ is in a dimension of 32.
j) The SE-ResNeXt-CAN network model is trained to acquire an optimized SE-ResNeXt-CAN network model.
k) batches, each batch including k) A new ECG signal dataset is divided into T signals forming ECG signal set Y, Y={$Y_1, Y_2, \ldots, Y_i, \ldots, Y_N$}, where $Y_i$ denotes an i-th ECG signal, i∈{1, . . . , T}
n) The i-th ECG signal Y is input into the optimized SE-ResNeXt-CAN network model to acquire feature $f^{5'}$, where the feature includes 512 channels, and is in a dimension of 40. A second multilayer perceptron is constructed, including a flattening layer, a first fully connected layer, a rectified linear unit (Relu) activation function layer, and a second fully connected layer in sequence. The feature $f^{5'}$ is input into the second multilayer perceptron to acquire feature $f^{5''}$. The feature $f^{5''}$ is input into a softmax activation function to acquire probability distribution $z_i$ of the i-th ECG signal $Y_i$, where the probability distribution $z_i$ is a classification result of the ECG signal. The first fully connected layer in the second multilayer perceptron includes 16 neurons, and the second fully connected layer in the second multilayer perceptron includes 9 neurons.

The SE-ResNeXt-CAN network model includes a shallow feature extraction module, a first SERM, a second SERM, a first CARM, and a second CARM. The SERM includes a RM and an excitation and convolution module in parallel. The RM can easily learn identity mapping, which accelerates the convergence speed of the network. The SE module models the global information of the feature map, effectively mining the channel correlation between features and improving the feature expression ability. The SE module is combined with the convolutional layer to weight importance of the feature while extracting the feature, further enhancing the feature expression ability and improving model performance. The CARM includes a dilated convolution module, a RM, and a channel attention module in parallel. The dilated convolution module expands the receptive field and can extract rich context information. The RM helps network training and optimizes the deep structure. The channel attention module can improve the feature expression ability and generalization ability of the network.

In an embodiment of the present disclosure, in the step a), the ECG signal dataset is a PTB-XL dataset, and the T signals in each batch are sampled at a rate of 500 Hz, with duration of 10 s.

In an embodiment of the present disclosure, the step b) is as follows.
- b-1) Gaussian noise with a mean of 0, a variance of 0.01, and a same size as the i-th ECG signal $X_i$ is generated by an np.random.normal function in Python.
- b-2) The Gaussian noise is added to the i-th ECG signal $X_i$ to acquire the sample $X_i^{M1}$.

The step d) is as follows.
- d-1) The shallow feature extraction module of the SE-ResNeXt-CAN network model is constructed, including a convolutional layer, a Batch_Norm layer, a Relu activation function, and a Dropout layer in sequence. The sample $X_i^{M1}$ is input into the shallow feature extraction module to acquire the feature $f^1$. In the shallow feature extraction module, the convolutional layer includes 32 channels and a convolutional kernel with a size of 3, a stride of 2, and a padding of 1. In the Dropout layer, the probability is 0.5. The feature $f^1$ includes 32 channels, and is in a dimension of 2,500.

In an embodiment of the present disclosure, the step e) is as follows.
- e-1) The first SERM of the SE-ResNeXt-CAN network model is constructed, including a RM and an excitation and convolution module.
- e-2) The RM of the first SERM is constructed, including a first branch and a second branch. The first branch of the RM is constructed, including a first convolutional layer, a second convolutional layer, a first batch normalization (BN) layer, a Relu activation function, a third convolutional layer, a second BN layer, and a Dropout layer in sequence. The feature $f^1$ is input into the first branch of the RM to acquire feature. The second branch of the RM is constructed, including a max pooling layer and a convolutional layer in sequence. The feature $f^1$ is input into the second branch of the RM to acquire feature $f_2^2$. The feature $f_1^2$ and the feature $f_2^2$ are added to acquire feature $rm^1$. In the first branch, the first convolutional layer includes 64 channels and a convolutional kernel with a size of 3, a stride of 2, and a padding of 1. The second convolutional layer includes 64 channels and a convolutional kernel with a size of 3, a stride of 2, and a padding of 1. The third convolutional layer includes 64 channels and a convolutional kernel with a size of 3, a stride of 1, and a padding of 1. In the first branch, the Dropout layer has a probability of 0.5. In the second branch, the convolutional layer includes 64 channels and a convolutional kernel with a size of 3, a stride of 2, and a padding of 1. In the second branch, the max pooling layer has a pooling window of 2.
- e-3) The excitation and convolution module is constructed, including a first convolutional layer, a first SE module, a second convolutional layer, a second SE module, a third convolutional layer, and a third SE module in sequence. The feature $f^1$ is input into the excitation and convolution module to acquire feature $f_3^2$. In the excitation and convolution module, the first convolutional layer includes 64 channels and a convolutional kernel with a size of 3, a stride of 2, and a padding of 1. In the excitation and convolution module, the second convolutional layer includes 64 channels and a convolutional kernel with a size of 3, a stride of 2, and a padding of 1. In the excitation and convolution module, the third convolutional layer includes 64 channels and a convolutional kernel with a size of 3, a stride of 1, and a padding of 1.
- e-4) The feature $rm^1$ and the feature $f_3^2$ are added to acquire the feature $f^2$. The feature $f^2$ includes 64 channels, and is in a dimension of 625.

In an embodiment of the present disclosure, the step f) is as follows.
- f-1) The second SERM of the SE-ResNeXt-CAN network model is constructed, including a RM and an excitation and convolution module.
- f-2) The RM of the second SERM is constructed, including a first branch and a second branch. The first branch of the RM is constructed, including a first convolutional layer, a second convolutional layer, a first batch normalization (BN) layer, a Relu activation function, a third convolutional layer, a second BN layer, and a Dropout layer in sequence. The feature $f^2$ is input into the first branch of the RM to acquire a feature $f_1^3$. The second branch of the RM is constructed, including a max pooling layer and a convolutional layer in sequence. The feature $f^2$ is input into the second branch of the RM to acquire feature $f_2^3$ The feature $f_1^3$ and the feature $f_2^3$ are added to acquire feature $rm^2$. In the first branch, the first convolutional layer includes 128 channels and a convolutional kernel with a size of 3, a stride of 2, and a padding of 1. The second convolutional layer includes 128 channels and a convolutional kernel with a size of 3, a stride of 2, and a padding of 1. The third convolutional layer includes 128 channels and a convolutional kernel with a size of 3, a stride of 1, and a padding of 1. In the first branch, the Dropout layer has a probability of 0.5. In the second branch, the convolutional layer includes 128 channels and a convolutional kernel with a size of 3, a stride of 2, and a padding of 2. In the second branch, the max pooling layer has a pooling window of 2.
- f-3) The excitation and convolution module is constructed, including a first convolutional layer, a first SE module, a second convolutional layer, a second SE module, a third convolutional layer, and a third SE module in sequence. The feature $f^2$ is input into the excitation and convolution module to acquire feature $f_3^3$. In the excitation and convolution module, the first convolutional layer includes 128 channels and a convolutional kernel with a size of 3, a stride of 2, and a padding of 1. In the excitation and convolution module, the second convolutional layer includes 128 channels and a convolutional kernel with a size of 3, a stride of 2, and a padding of 1. In the excitation and convolution module, the third convolutional layer includes 128 channels and a convolutional kernel with a size of 3, a stride of 1, and a padding of 1.
- f-4) The feature $rm^2$ and the feature $f_3^3$ are added to acquire the feature $f^3$. The feature $f^3$ includes 128 channels, and is in a dimension of 157.

In an embodiment of the present disclosure, the step g) is as follows.
- g-1) The first CARM of the SE-ResNeXt-CAN network model is constructed, including a RM, a dilated convolution module, and a channel attention module.
- g-2) The RM of the first CARM is constructed, including a first branch and a second branch. The first branch of the RM is constructed, including a first convolutional layer, a BN layer, a first Relu activation function, a second convolutional layer, a second Relu activation function, and a Dropout layer in sequence. The feature $f^3$ is input into the first branch of the RM to acquire feature $f_1^4$. The second branch of the RM is constructed, including a convolutional layer. The feature $f^3$ is input into the second branch of the RM to acquire feature $f_2^4$. The feature $f_1^4$ and the feature $f_2^4$ are added to acquire feature $rm^3$. In the first branch, the first convolutional layer includes 256 channels and a convolutional kernel with a size of 3, a stride of 2, and a padding of 1. In the first branch, the second convolutional layer includes 256 channels and a convolutional kernel with a size of 3, a stride of 1, and a padding of 1.

g-3) The dilated convolution module of the first CARM is constructed, including a first dilated convolution layer, a first convolutional layer, a second dilated convolution layer, a second convolutional layer, and a Relu activation function in sequence. The feature $f^3$ is input into the dilated convolution module to acquire feature $f_3^4$. The feature $rm^3$ and the feature $f_3^4$ are added to acquire feature $pcdc^1$. In the dilated convolution module, the first dilated convolution layer includes 256 channels and a convolutional kernel with a size of 5, a dilation rate of 2, a stride of 1, and a padding of 4. In the dilated convolution module, the second dilated convolution layer includes 256 channels and a convolutional kernel with a size of 5, a dilation rate of 2, a stride of 1, and a padding of 4. In the dilated convolution module, the first convolutional layer includes 256 channels and a convolutional kernel with a size of 3, a stride of 2, and a padding of 1. In the dilated convolution module, the second convolutional layer includes 256 channels and a convolutional kernel with a size of 3, a stride of 1, and a padding of 1.

g-4) The channel attention module of the first CARM is constructed, including a convolutional layer, an average pooling layer, a first fully connected layer, and a second fully connected layer in sequence. The feature $f^3$ is input into the channel attention module to acquire feature $f_4^4$. In the channel attention module, the convolutional layer includes 256 channels and a convolutional kernel with a size of 1 and a stride of 1. In the channel attention module, the average pooling layer includes has a pooling window of 157. In the channel attention block, the first fully connected layer includes 64 neurons, and the second fully connected layer includes 1 neuron.

g-5) The feature $pcdc^1$ is multiplied by the feature $f_4^4$ to acquire the feature $f^4$. The feature $f^4$ includes 256 channels, and is in a dimension of 79.

In an embodiment of the present disclosure, the step h) is as follows.

h-1) The second CARM of the SE-ResNext-CAN network model is constructed, including a RM, a dilated convolution module, and a channel attention module.

h-2) The RM of the second CARM is constructed, including a first branch and a second branch. The first branch of the RM is constructed, including a first convolutional layer, a BN layer, a first Relu activation function, a second convolutional layer, a second Relu activation function, and a Dropout layer in sequence. The feature $f^4$ is input into the first branch of the RM to acquire feature $f_1^5$. The second branch of the RM is constructed, including a convolutional layer. The feature $f^4$ is input into the second branch of the RM to acquire feature $f_2^5$. The feature $f_1^5$ and the feature $f_2^5$ are added to acquire feature $rm^4$. In the first branch, the first convolutional layer includes 512 channels and a convolutional kernel with a size of 3, a stride of 2, and a padding of 1. In the first branch, the second convolutional layer includes 512 channels and a convolutional kernel with a size of 3, a stride of 1, and a padding of 1. In the second branch, the convolutional layer includes 512 channels and a convolutional kernel with a size of 3, a stride of 2, and a padding of 1.

h-3) The dilated convolution module of the second CARM is constructed, including a first dilated convolution layer, a first convolutional layer, a second dilated convolution layer, a second convolutional layer, and a Relu activation function in sequence. The feature $f^4$ is input into the dilated convolution module to acquire feature $f_3^5$. The feature $rm^4$ and the feature $f_3^5$ are added to acquire feature $pcdc^2$. In the dilated convolution module, the first dilated convolution layer includes 512 channels and a convolutional kernel with a size of 5, a dilation rate of 2, a stride of 1, and a padding of 4. In the dilated convolution module, the second dilated convolution layer includes 512 channels and a convolutional kernel with a size of 5, a dilation rate of 2, a stride of 1, and a padding of 4. In the dilated convolution module, the first convolutional layer includes 512 channels and a convolutional kernel with a size of 3, a stride of 2, and a padding of 1. In the dilated convolution module, the second convolutional layer includes 512 channels and a convolutional kernel with a size of 3, a stride of 1, and a padding of 1.

h-4) The channel attention module of the second CARM is constructed, including a convolutional layer, an average pooling layer, a first fully connected layer, and a second fully connected layer in sequence. The feature $f^4$ is input into the channel attention module to acquire feature $f_4^5$. In the channel attention module, the convolutional layer includes 512 channels and a convolutional kernel with a size of 1 and a stride of 1. In the channel attention module, the average pooling layer includes has a pooling window of 79. In the channel attention block, the first fully connected layer includes 128 neurons, and the second fully connected layer includes 1 neuron.

h-5) The feature $pcdc^2$ is multiplied by the feature $f_4^5$ to acquire the $f^5$ feature. The feature $f^5$ includes 512 channels, and is in a dimension of 40.

In an embodiment of the present disclosure, in the step j), the SE-ResNeXt-CAN network model is trained by an adaptive moment estimation (Adam) optimizer through an NT-Xent loss function to acquire the optimized SE-ResNeXt-CAN network model.

In an embodiment of the present disclosure, in the step k), the new ECG signal dataset is a China Physiological Signal Challenge (CPSC) dataset, and the T signals in each batch are sampled at a rate of 500 Hz, with duration of 10 s. There are 9 classes in the CPSC dataset.

Figure 4:
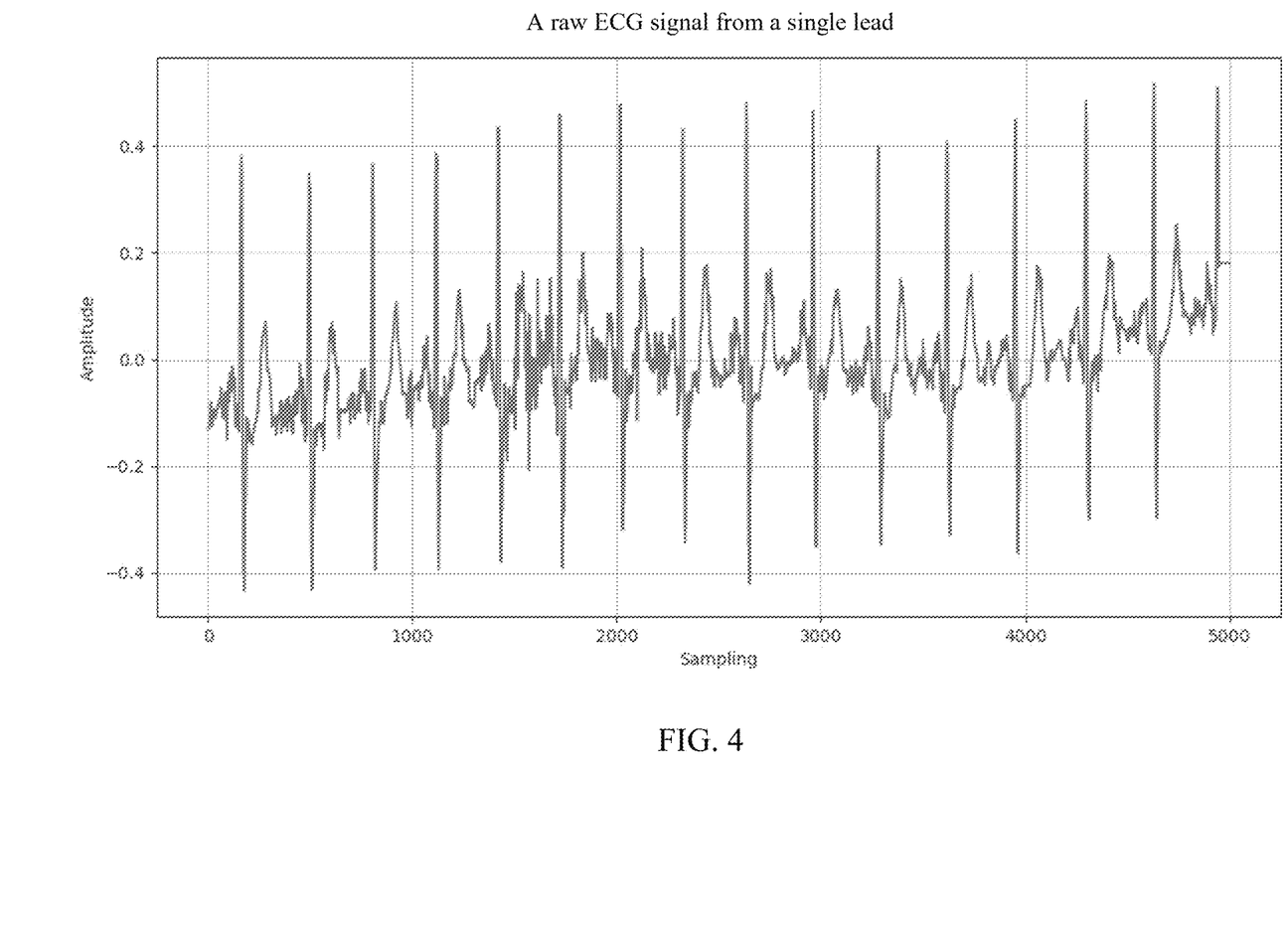
FIG. 4 shows a raw ECG signal.
Figure 5:
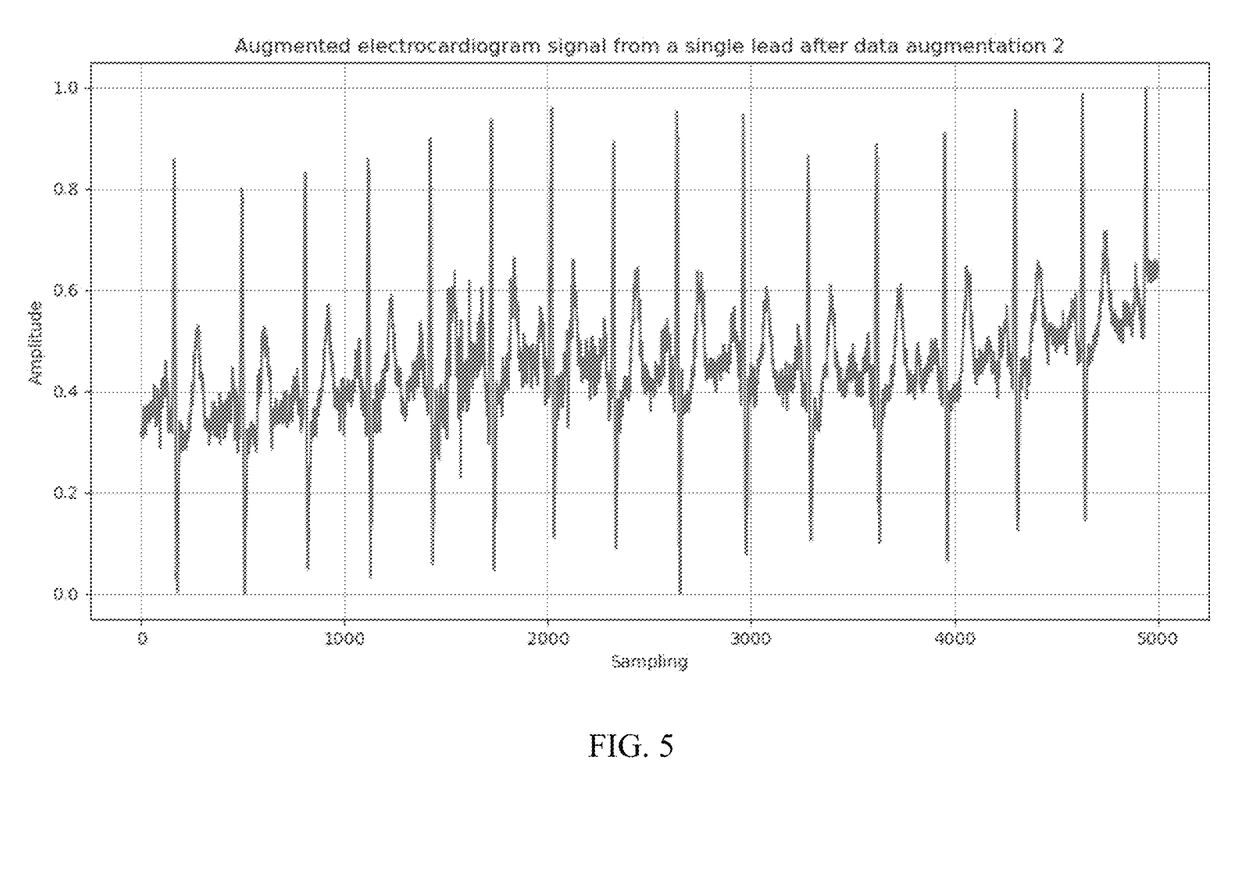
FIG. 5 shows an ECG signal after a random augmentation.
Figure 6A:
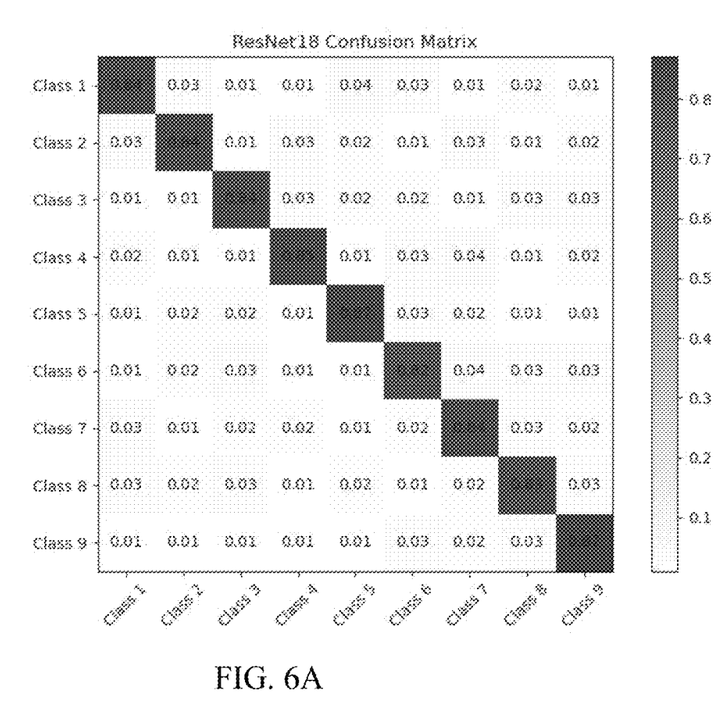
FIGS. 6A-6E show confusion matrixes for each model.
Figure 6B:
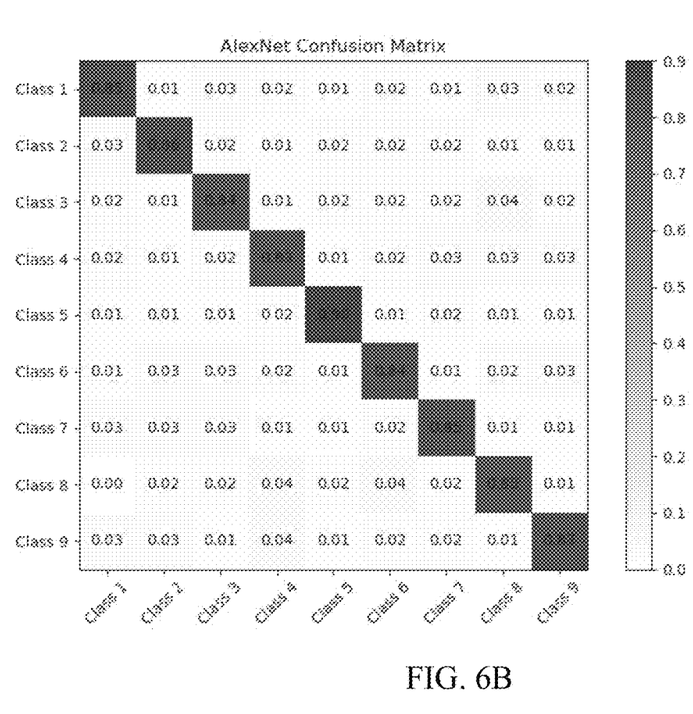
Figure 6C:
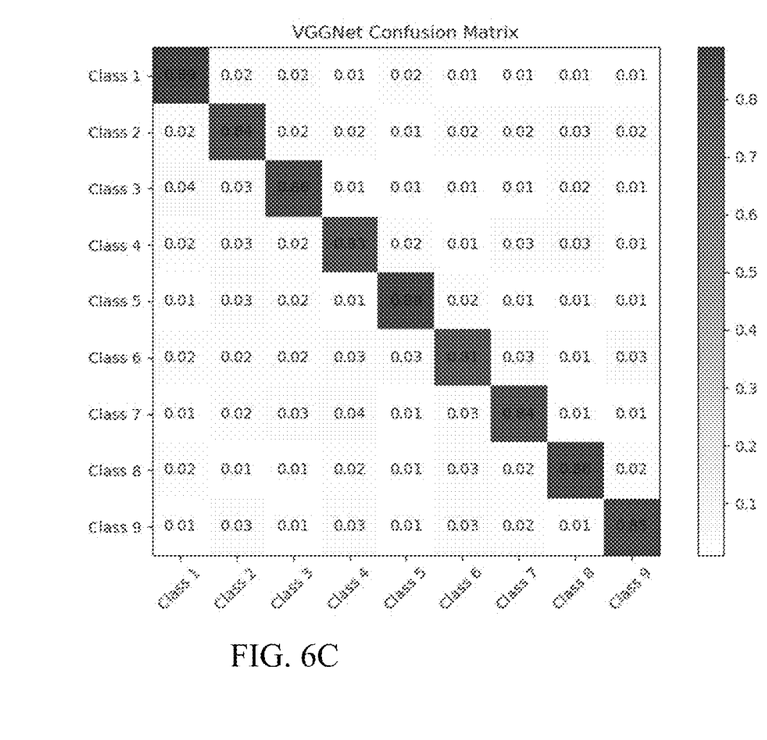
Figure 6D:
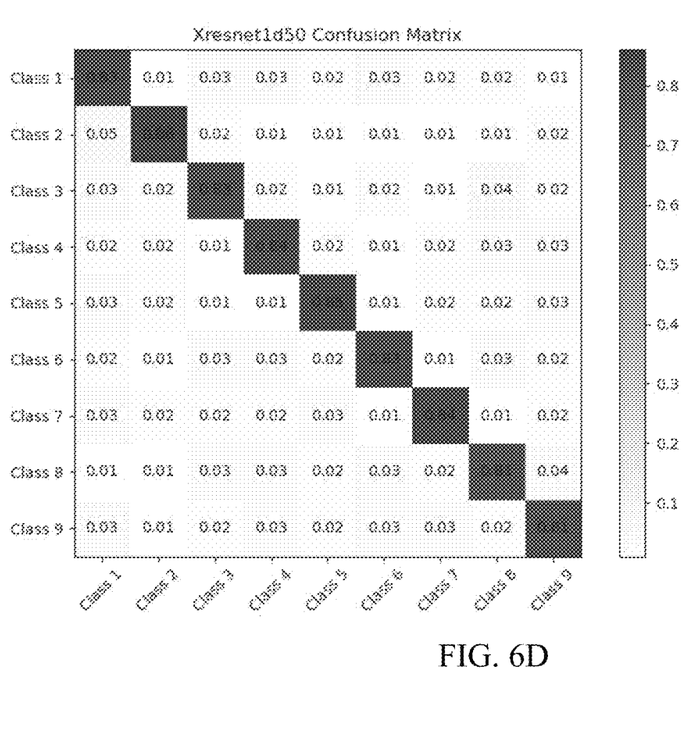
Figure 6E:
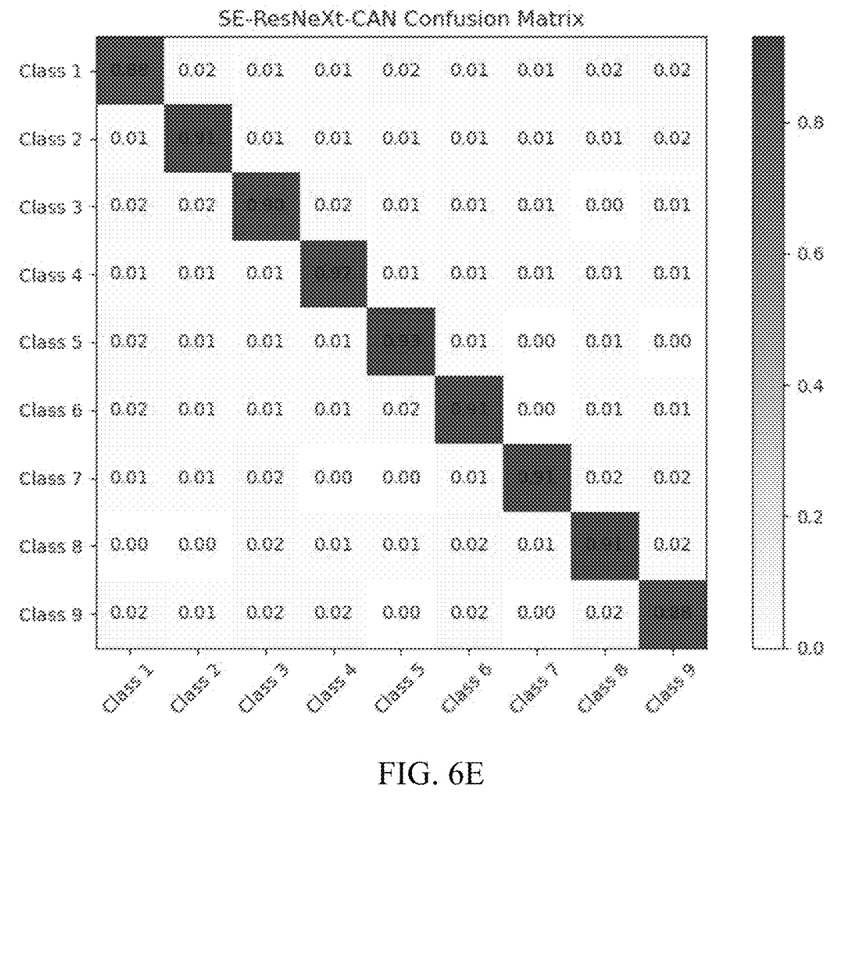

(1) Contrastive learning relies on data augmentation. FIG. 4 shows a raw ECG signal, and FIG. 5 shows an ECG signal after a random augmentation. This comparative display is helpful to the understanding of the impact of data augmentation on ECG signal processing.

(2) In order to evaluate the performance of the proposed model when it is transferred from one task to another, a comparative experiment on transferability evaluation was conducted on two datasets. The experimental results are shown in Table 1. Table 1 shows Transferability Evaluation Results (AUROC).

(3) In order to evaluate the accuracy of the model in prediction, a comparative experiment of linear evaluation was conducted on two datasets. The experimental results are shown in Table 2. Table 2 shows Linear Evaluation Results (AUROC).

(4) In order to comprehensively evaluate the performance of the classification models, confusion matrices for different models are provided. Due to the influence of floating point numbers, there may be some errors in the experimental results, as shown in FIGS. 6A-6E.

Figure 7:
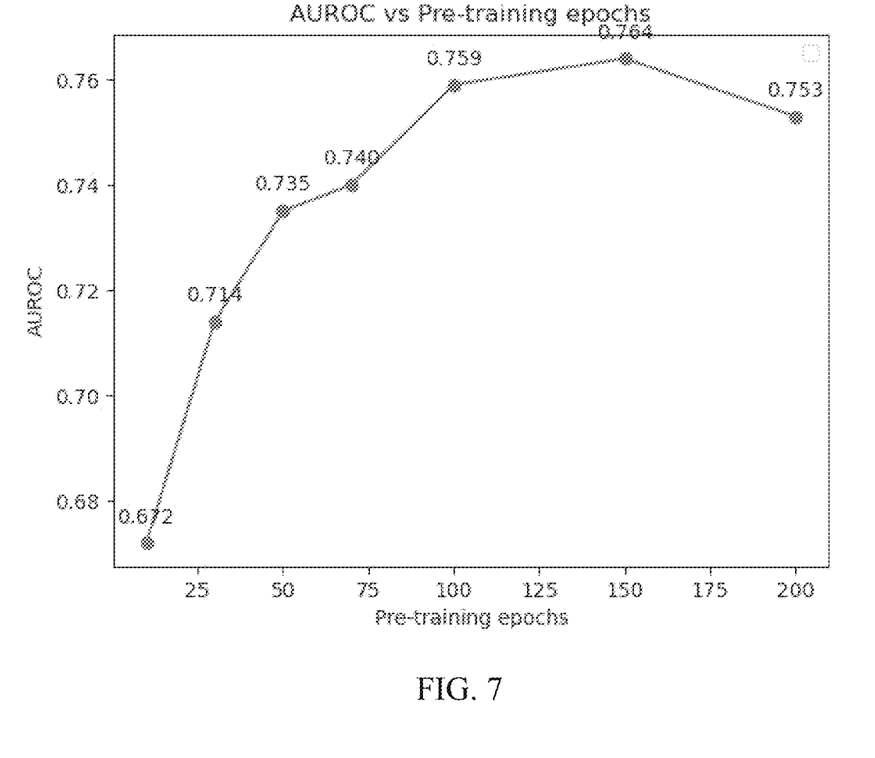
FIG. 7 shows pre-training epoch ablation experiment results on PTB-XL dataset (AUROC).
Figure 8:
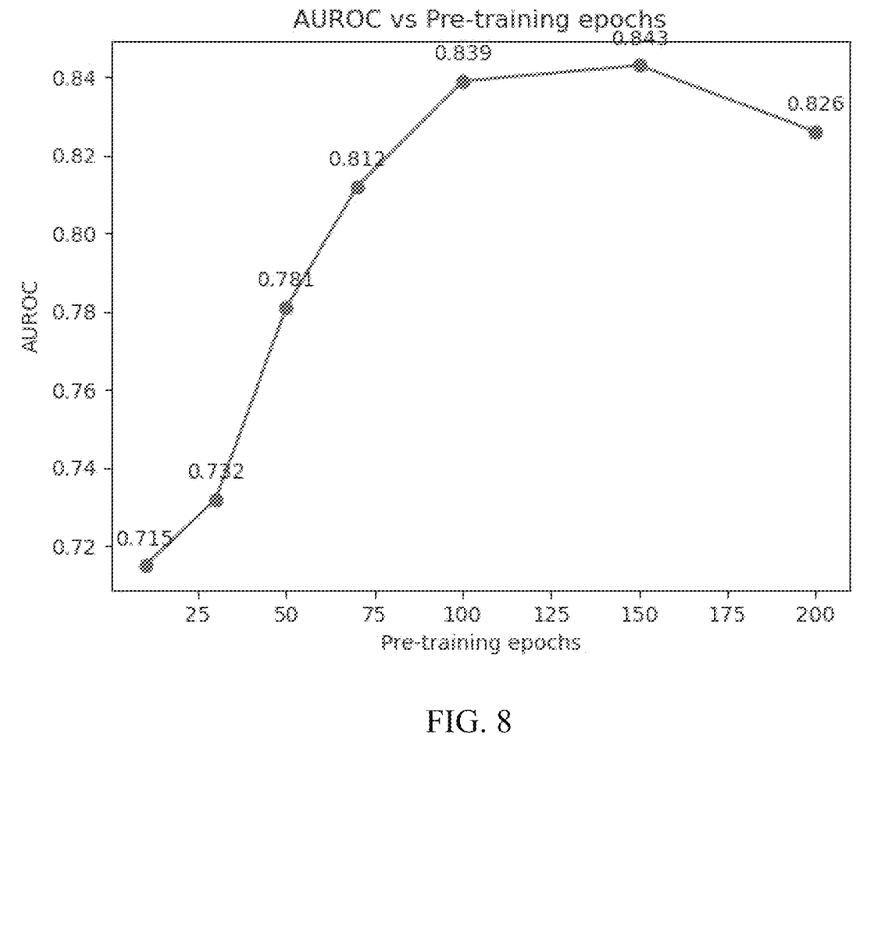
FIG. 8 shows pre-training epoch ablation experiment results on CPSC dataset (AUROC).

(5) In order to verify the influence of the number of pre-training epochs on the experimental results, ablation experiments were conducted on the number of pre-training epochs. The experimental results are shown in FIGS. 7 and 8.

Finally, it should be noted that the above descriptions are only preferred embodiments of the present disclosure, and are not intended to limit the present disclosure. Although the present disclosure has been described in detail with reference to the foregoing embodiments, those skilled in the art may still modify the technical solutions described in the foregoing embodiments, or equivalently substitute some technical features thereof. Any modification, equivalent substitution, improvement, etc. within the spirit and principles of the present disclosure shall fall within the scope of protection of the present disclosure.

What is claimed is:

1. An electrocardiogram (ECG) signal classification method based on contrastive learning and multi-scale feature extraction, comprising the following steps:
   a) dividing an ECG signal dataset into K batches, each of the K batches comprising T signals forming an ECG signal set X, $X=\{X_1, X_2, \ldots, X_i, \ldots, X_T\}$, wherein $X_i$ denotes an i-th ECG signal, $i \in \{1, \ldots, T\}$;
   b) performing data augmentation on the i-th ECG signal $X_i$ to acquire a sample $X_i^{M1}$;
   c) constructing a squeeze-and-excitation-residual network with next-generation aggregated transformations-context-aware network (SE-ResNeXt-CAN) network model, comprising a shallow feature extraction module, a first squeeze-and-excitation residual module (SERM), a second SERM, a first context-aware residual module (CARM), and a second CARM, wherein the residual network is constructed such that the first SERM receives an output of the shallow feature extraction module as an input, the second SERM receives an output of the first SERM as an input, the first CARM receives an output of the second SERM as an input, and the second CARM receives an output of the first CARM as an input;
   d) inputting the sample $X_i^{M1}$ into the shallow feature extraction module of the SE-ResNeXt-CAN network model to acquire a feature $f^1$;
   e) inputting the feature $f^1$ into the first SERM of the SE-ResNeXt-CAN network model to acquire a feature $f^2$;
   f) inputting the feature $f^2$ into the second SERM of the SE-ResNeXt-CAN network model to acquire a feature $f^3$;
   g) inputting the feature $f^3$ into the first CARM of the SE-ResNeXt-CAN network model to acquire a feature $f^4$;
   h) inputting the feature $f^4$ into the second CARM of the SE-ResNeXt-CAN network model to acquire a feature $f^5$;
   i) constructing a first multilayer perceptron, comprising a flattening layer, a first fully connected layer, and a second fully connected layer in sequence; and inputting the feature $f^5$ into the first multilayer perceptron to acquire a feature $h_i$;
   j) training the SE-ResNeXt-CAN network model to acquire an optimized SE-ResNeXt-CAN network model;
   k) dividing a new ECG signal dataset into K batches, each of the K batches comprising T signals forming an ECG signal set Y, $Y=\{Y_1, Y_2, \ldots, Y_i, \ldots, Y_N\}$ wherein $Y_i$ denotes an i-th ECG signal, $i \in \{1, \ldots, T\}$; and
   n) inputting the i-th ECG signal $Y_i$ into the optimized SE-ResNeXt-CAN network model to acquire a feature $f^{5'}$; constructing a second multilayer perceptron, comprising a flattening layer, a first fully connected layer, a rectified linear unit (Relu) activation function layer, and a second fully connected layer in sequence; inputting the feature $f^{5'}$ into the second multilayer perceptron to acquire a feature $f^{5''}$; and inputting the feature $f^{5''}$ into a softmax activation function to acquire a probability distribution $z_i$ of the i-th ECG signal $Y_i$, wherein the probability distribution $z_i$ is a classification result of the ECG signal;

wherein the step d) comprises:
   d-1) constructing the shallow feature extraction module of the SE-ResNeXt-CAN network model, comprising a convolutional layer, a Batch_Norm layer, a Relu activation function, and a Dropout layer in sequence; and inputting the sample $X_i^{M1}$ into the shallow feature extraction module to acquire the feature $f^1$;

wherein the step e) comprises:
   e-1) constructing the first SERM of the SE-ResNeXt-CAN network model, comprising a residual module (RM) and an excitation and convolution module;
   e-2) constructing the RM of the first SERM, comprising a first branch and a second branch; constructing the first branch of the RM, comprising a first convolutional layer, a second convolutional layer, a first batch normalization (BN) layer, a Relu activation function, a third convolutional layer, a second BN layer, and a Dropout layer in sequence; inputting the feature $f^1$ into the first branch of the RM to acquire a feature $f_1^2$; constructing the second branch of the RM, comprising a max pooling layer and a convolutional layer in sequence; inputting the feature $f^1$ into the second branch of the RM to acquire a feature $f_2^2$; and adding the feature $f_1^2$ and the feature $f_2^2$ to acquire a feature $rm^1$;
   e-3) constructing the excitation and convolution module, comprising a first convolutional layer, a first SE module, a second convolutional layer, a second SE module, a third convolutional layer, and a third SE module in sequence; and inputting the feature $f^1$ into the excitation and convolution module to acquire a feature $f_3^2$; and
   e-4) adding the feature $rm^1$ and the feature $f_3^2$ to acquire the feature $f^2$;

wherein the step f) comprises:
   f-1) constructing the second SERM of the SE-ResNeXt-CAN network model, comprising a RM and an excitation and convolution module;
   f-2) constructing the RM of the second SERM, comprising a first branch and a second branch; constructing the first branch of the RM, comprising a first convolutional layer, a second convolutional layer, a first BN layer, a Relu activation function, a third convolutional layer, a second BN layer, and a Dropout layer in sequence; inputting the feature $f^2$ into the first branch of the RM to acquire a feature $f_1^3$; constructing the second branch of the RM, comprising a max pooling layer and a convolutional layer in sequence; inputting the feature $f^2$ into the second branch of the RM to acquire a feature $f_2^3$; and adding the feature $f_1^3$ and the feature $f_2^3$ to acquire a feature $rm^2$;

f-3) constructing the excitation and convolution module, comprising a first convolutional layer, a first SE module, a second convolutional layer, a second SE module, a third convolutional layer, and a third SE module in sequence; and inputting the feature $f^2$ into the excitation and convolution module to acquire a feature $f_3^3$; and f-4) adding the feature $rm^2$ and the feature $f_3^3$ to acquire the feature $f^3$;

wherein the step g) comprises:

g-1) constructing the first CARM of the SE-ResNeXt-CAN network model, comprising a RM, a dilated convolution module, and a channel attention module;

g-2) constructing the RM of the first CARM, comprising a first branch and a second branch; constructing the first branch of the RM, comprising a first convolutional layer, a BN layer, a first Relu activation function, a second convolutional layer, a second Relu activation function, and a Dropout layer in sequence; inputting the feature $f^3$ into the first branch of the RM to acquire a feature $f_1^4$; constructing the second branch of the RM, comprising a convolutional layer; inputting the feature $f^3$ into the second branch of the RM to acquire a feature $f_2^4$; adding the feature $f_1^4$ and the feature $f_2^4$ to acquire a feature $rm^3$;

g-3) constructing the dilated convolution module of the first CARM, comprising a first dilated convolution layer, a first convolutional layer, a second dilated convolution layer, a second convolutional layer, and a Relu activation function in sequence; inputting the feature $f^3$ into the dilated convolution module to acquire a feature $f_3^4$; and adding the feature $rm^3$ and the feature $f_3^4$ to acquire a feature $pcdc^1$;

g-4) constructing the channel attention module of the first CARM, comprising a convolutional layer, an average pooling layer, a first fully connected layer, and a second fully connected layer in sequence; and inputting the feature $f^3$ into the channel attention module to acquire a feature $f_4^4$; and g-5) multiplying the feature $pcdc^1$ by the feature $f_4^4$ to acquire the feature $f^4$;

wherein the step h) comprises:

h-1) constructing the second CARM of the SE-ResNeXt-CAN network model, comprising a RM, a dilated convolution module, and a channel attention module;

h-2) constructing the RM of the second CARM, comprising a first branch and a second branch; constructing the first branch of the RM, comprising a first convolutional layer, a BN layer, a first Relu activation function, a second convolutional layer, a second Relu activation function, and a Dropout layer in sequence; inputting the feature $f^4$ into the first branch of the RM to acquire a feature $f_1^5$; constructing the second branch of the RM, comprising a convolutional layer; inputting the feature $f^4$ into the second branch of the RM to acquire a feature $f_2^5$; adding the feature $f_1^5$ and the feature $f_2^5$ to acquire a feature $rm^4$;

h-3) constructing the dilated convolution module of the second CARM, comprising a first dilated convolution layer, a first convolutional layer, a second dilated convolution layer, a second convolutional layer, and a Relu activation function in sequence; inputting the feature $f^4$ into the dilated convolution module to acquire a feature $f_3^5$; and adding the feature $rm^4$ and the feature $f_3^5$ to acquire a feature $pcdc^2$;

h-4) constructing the channel attention module of the second CARM, comprising a convolutional layer, an average pooling layer, a first fully connected layer, and a second fully connected layer in sequence; and inputting the feature $f^4$ into the channel attention module to acquire a feature $f_4^5$; and h-5) multiplying the feature $pcdc^2$ by the feature $f_4^5$ to acquire the feature $f^5$.

2. The ECG signal classification method based on the contrastive learning and the multi-scale feature extraction according to claim 1, wherein in the step a), the ECG signal dataset is a PTB-XL dataset, and the T signals in each of the K batches are sampled at a rate of 500 Hz, with duration of 10 s.

3. The ECG signal classification method based on the contrastive learning and the multi-scale feature extraction according to claim 1, wherein the step b) comprises:

b-1) generating, by an np.random.normal function in Python, Gaussian noise with a mean of 0, a variance of 0.01, and a same size as the i-th ECG signal $X_i$; and b-2) adding the Gaussian noise to the i-th ECG signal $X_i$ to acquire the sample $X_i^{M1}$.

4. The ECG signal classification method based on the contrastive learning and the multi-scale feature extraction according to claim 1, wherein the step j) comprises: training, by an adaptive moment estimation (Adam) optimizer, the SE-ResNeXt-CAN network model through an NT-Xent loss function to acquire the optimized SE-ResNeXt-CAN network model.

5. The ECG signal classification method based on the contrastive learning and the multi-scale feature extraction according to claim 1, wherein in the step k), the new ECG signal dataset is a China Physiological Signal Challenge (CPSC) dataset, and the signals in each of the batches are sampled at a rate of 500 Hz, with duration of 10 s.

* * * * *